United States Patent
Bruder (10) Patent No.: US 7,664,221 B2
(45) Date of Patent: Feb. 16, 2010

(54) METHOD AND COMPUTED TOMOGRAPHY UNIT FOR PRODUCING COMPUTED TOMOGRAMS OF A PATIENT'S BEATING HEART

(75) Inventor: Herbert Bruder, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 183 days.

(21) Appl. No.: 11/377,887

(22) Filed: Mar. 17, 2006

(65) Prior Publication Data
US 2007/0086563 A1 Apr. 19, 2007

(30) Foreign Application Priority Data
Mar. 18, 2005 (DE) .................. 10 2005 012 653

(51) Int. Cl.
*A61B 6/03* (2006.01)
(52) U.S. Cl. .................. 378/4; 378/8; 378/901
(58) Field of Classification Search .......... 378/4, 378/8, 901, 131; 382/131
See application file for complete search history.

(56) References Cited

U.S. PATENT DOCUMENTS

| | | | | |
|---|---|---|---|---|
| 6,061,422 | A * | 5/2000 | Miyazaki et al. | 378/15 |
| 6,078,639 | A * | 6/2000 | Heuscher | 378/15 |
| 6,421,412 | B1 * | 7/2002 | Hsieh et al. | 378/9 |
| 6,526,117 | B1 * | 2/2003 | Okerlund et al. | 378/8 |
| 6,529,575 | B1 * | 3/2003 | Hsieh | 378/4 |
| 6,665,370 | B2 | 12/2003 | Bruder et al. | |
| 6,678,346 | B2 * | 1/2004 | Hsieh | 378/4 |
| 6,947,584 | B1 * | 9/2005 | Avila et al. | 382/131 |
| 2003/0072419 | A1 * | 4/2003 | Bruder et al. | 378/210 |
| 2003/0128801 | A1 * | 7/2003 | Eisenberg et al. | 378/19 |
| 2004/0114708 | A1 * | 6/2004 | Bruder et al. | 378/4 |
| 2004/0131140 | A1 * | 7/2004 | Bruder et al. | 378/4 |
| 2004/0170246 | A1 * | 9/2004 | Koenig et al. | 378/4 |
| 2004/0208276 | A1 * | 10/2004 | Kaufman | 378/4 |
| 2005/0058248 | A1 * | 3/2005 | Klingenbeck-Regn | 378/95 |
| 2005/0169424 | A1 * | 8/2005 | Bruder et al. | 378/95 |

(Continued)

FOREIGN PATENT DOCUMENTS

DE 101 33 237 A1 7/2001

(Continued)

OTHER PUBLICATIONS

Stierstorfer et al., Segmented multiple plane reconstruction: a novel approximate reconstruction scheme for multi-slice spiral CT, 2002, Phys. Med. Biol., pp. 2571-2581.*

(Continued)

*Primary Examiner*—Edward J Glick
*Assistant Examiner*—John M Corbett
(74) *Attorney, Agent, or Firm*—Harness Dickey & Pierce, P.L.C.

(57) ABSTRACT

A method and computed tomography unit are disclosed for producing computed tomograms of a patient's beating heart by voxelwise reconstruction of volume data records from prescribed cardiac cycle phases. Firstly, a multiplicity of voxelwise partial reconstructions are calculated from projection segments substantially smaller than 180° in accordance with small cardiac phase segments. The complete voxel data that cover overall at least 180° and originate from a preselected cardiac phase are subsequently summed up per cardiac phase to be considered from the pool of the incomplete reconstructed voxel data.

28 Claims, 4 Drawing Sheets

U.S. PATENT DOCUMENTS

2006/0140338 A1\* 6/2006 Bruder et al. .................. 378/15

FOREIGN PATENT DOCUMENTS

WO    WO2004/070661 A1 \* 8/2004

OTHER PUBLICATIONS

Flohr et al., Heart Rate Adaptive Optimization of Spiral and Temporal Resolution for Electrocardiogram-Gated Multislice Spiral CT of the Heart, 2001, Journal of Computer Assisted Tomography, vol. 27, No. 6, pp. 907-923.\*

Flohr et al., First performance evaluation of a dual-source CT (DSCT) system, Dec. 10, 2005, European Radiology, vol. 16, No. 2, pp. 256-268.\*

Taguchi et al., High temporal resolution for multislice helical computed tomography, May 2000, Medical Physics, vol. 27, No. 5, pp. 861-872.\*

Sourbelle, Performance Evaluation of Exact and Approximate Cone-beam Algorithms in Spiral Computed Tomography, Mar. 25, 2002, Erlangen University, Dissertation.\*

Lembcke et al., Segmented Reconstruction, Visions Magazine, 2002, No. 2, vol. 2, pp. 42-44.\*

Stierstorfer et al., A data Compression Scheme for the SMPR Algorithm for Multislice Spiral CT, Jul. 1, 2003, Proceedings of the VIIth International Conference on Fully 3D Reconstruction in Radiology and Nuclear Medicine, Saint Malo, France, pp. 155-156.\*

Flohr et al., A retrospectively ECG-gated multislice spiral CT scan and reconstruction technique with suppression of heart pulsation artifacts for cardio-thoracic imaging with extended volume coverage, 2002, European Radiology, vol. 12, pp. 1497-1503.\*

Turbell, Cone-Beam Reconstruction Using Filtered Backprojection, Feb. 2001, Linkoping Studies in Science and Technology dissertation No. 672.\*

Kachelriess et al., 4D Reconstruction for Wide Cone-Angle Medical CT, Oct. 19-25, 2003, 2003 IEEE Nuclear Science Symposium Conference Record, vol. 5, pp. 3248-3252.\*

Kak et al., Principles of Computerized Tomographic Imaging, 1988, IEEE Press, ISBN 0-87942-198-3, Chapter 3.\*

Bushberg et al., The Essential Physics of Medical Imaging, 2002, ISBN 0-683-30118-7, p. 329.\*

Flor Thomas, Ohnesorge Bernd, "Heart-Rate Adaptive Optimization of Spatial and Temporal Resolution for ECG-Gated Multislice Spiral CT of the Heart", Journal of Computer Assisted Tomography, 25(6): 907-923.

\* cited by examiner

METHOD AND COMPUTED TOMOGRAPHY UNIT FOR PRODUCING COMPUTED TOMOGRAMS OF A PATIENT'S BEATING HEART

The present application hereby claims priority under 35 U.S.C. §119 on German patent application number DE 10 2005 012 653.7 filed Mar. 18, 2005, the entire contents of which is hereby incorporated herein by reference.

FIELD

The invention generally relates to a method and computed tomography unit. For example, it may relate to one for producing computed tomograms of a patient's beating heart by voxelwise reconstruction of volume data records from prescribed cardiac cycle phases.

BACKGROUND

Methods and computed tomography units are generally known from cardio CT. Reference may be made, for example, to the document by Thomas Flohr and Bernd Ohnesorge entitled "Heart-Rate Adaptive Optimization of Spatial and Temporal Resolution for ECG-Gated Multislice Spiral CT of the Heart", Journal of Computer Assisted Tomography, 25(6): 907-923. In this known method of CT cardiac imaging an ECG of the patient is recorded in parallel with the CT scan and is stored jointly with the acquired detector data. Detector data that are to be assigned to a specific cardiac phase can then be selected retrospectively with the aid of a typical ECG structure, for example an R wave, and a reconstruction of the image data can be carried out starting with a specific instant of the cycle relative to the R wave. This phase-resolved imaging of the cardiac volume is used both for coronary CT angiography and for functional diagnostics on the heart.

A multiplicity of images that show the overall cardiac cycle at different time intervals are required for functional diagnostics. Accordingly, volume data records are reconstructed at different initial instants relative to the subsequent R wave, the detector data used for the purpose extending, however, over a relatively large cardiac phase period. As a rule, even the data collection periods from which the individual temporally consecutive images are reconstructed overlap one another, because the temporal spacing at which the operator requires consecutive images of the heart is mostly smaller than the period from which the data for the reconstruction of the images must be collected.

Thus, at specific instants of the cardiac phase data records flow repeatedly into the reconstruction of volume data records of different initial instants, the result being a very large calculation volume.

SUMMARY

An object of at least one embodiment of the invention is for a method and/or a computed tomography unit for producing computed tomograms of a patient's beating heart that requires a reduced outlay on computation.

In at least one embodiment, the inventor has realized that it is possible to reduce the calculation volume substantially when calculating a temporal sequence of cardio CT pictures by not reconstructing each voxel or each group of voxels with the aid of a complete half revolution data record when reconstructing volume data records in voxelwise fashion, but by firstly partially reconstructing the individual voxels from small data segments and subsequently adding up so many subvoxels that their sum corresponds overall to a complete half revolution. It is possible thereby firstly to calculate a series of incomplete voxels (=subvoxels) or incomplete voxel groups in small phase segments in one or more cardiac cycles. It is subsequently possible, beginning with an arbitrary starting point in time, to add up a number of incomplete voxels advancing in time until their data volume corresponds to a half revolution. These computation operations are simple additions, if appropriate weighted additions, but it is substantially easier to carry them out than a complete reconstruction. If the voxel or the voxel group is now calculated starting from a further initial instant, all that is required is to have recourse to another group of subvoxels already precalculated and to carry out the same adding up.

If appropriate, when the next instant is situated a data segment later or earlier there is the possibility of removing from the already calculated final voxel one of the incomplete voxels originally incorporated, and of adding a new incomplete voxel on the other side—seen in terms of time. These operations are mathematically very simple and can be carried out at high speed. Of course, it is not only a single voxel that can be calculated with this approach: rather, groups of voxels can also be calculated, for example all the voxels of a specific slice plane or of a specific volume region.

Thus, the basic idea of at least one embodiment resides in dividing the rotary scanning of a voxel into small angular segments of selectable size, reconstructing each segment independently, and storing this reconstructed incomplete voxel in relation to its cardiac phase. Subsequently, the incomplete voxels referred to cardiac phase and voxel are added up, if appropriate in a weighted fashion, and converted by calculation into a complete voxel or a group of complete voxels.

In at least one embodiment, the inventor therefore proposes a method for producing computed tomograms of a patient's beating heart, having the following method steps:

at least one X-ray tube is rotated relative to the patient about the latter and about a system axis in order to scan the patient, a pulse-correlated clock signal of the patient is recorded in order to determine therefrom the cycle phase and the cycle of the heart, the attenuation of the X-rays during the rotation of the at least one X-ray tube is detected continuously by at least one detector, preferably at least one multirow detector, and is output as detector output data to a control and arithmetic logic unit, the scanning volume is divided into small three-dimensional volume elements (=voxels), and in relation to each voxel a search is made for beams, and detector output data generated therefrom, that intersect this voxel, incomplete voxel values are reconstructed from these voxel-referred detector output data, the detector data used per voxel reconstruction comprising as a whole merely a scanning segment that corresponds only to a fraction of a half revolution, each reconstructed incomplete voxel value is assigned a time stamp from which it is possible to determine the cycle phase and the cycle from which the voxel has been reconstructed, for the purpose of a first calculation of at least one complete voxel value from a first cardiac phase period, incomplete voxel values from this cardiac phase period are added up until the sum of the scanning segments of the voxel values corresponds to at least 180°, and for the purpose of a second calculation of at least one complete voxel value from a second cardiac phase period, incomplete voxel values are added up from this second cardiac phase period until the sum of the scanning segments of the voxels corresponds to at least 180°, the first cardiac phase period and the second cardiac phase period overlapping one another.

It is true that this inventive method, in at least one embodiment, firstly requires computational outlay on the reconstruction of all the subvoxels over the cardiac cycles. However, this need only be carried out once. Thus, a temporal sequence of volume data records for displaying the beating heart can very easily be produced by simply adding up the correct subvoxels. The computational outlay required therefore is then reduced drastically in sum.

It is now possible by applying the basic principle set forth above to carry out the volume display in accordance with different points of view. On the one hand, it is possible to select the incomplete voxel values that are combined to form a complete voxel value from a single cardiac cycle. Thus, the image data originate overall from a somewhat longer cycle phase of the heart. On the other hand, it is also possible to extract the incomplete voxel values that are combined to form a complete voxel value from at least two consecutive cardiac cycles. The total duration of the cardiac phase from which the image data are extracted is thereby halved, or reduced to a third when three consecutive cardiac cycles are used. The result is a higher time resolution, but this is countered by the fact that the heart is not necessarily located at exactly the identical site over a number of cardiac cycles, and so fuzziness of location can arise from a rotation of the patient.

It is, however, also possible to reconstruct the incomplete voxel values themselves from detector data of only one cardiac cycle or, on the other hand, to reconstruct the incomplete voxel values from detector data of a number of consecutive cardiac cycles. The temporal resolution is also fundamentally reduced thereby once again when use is made of detector data from a number of cardiac cycles, there being a rise in the risk of fuzziness of movement owing to a movement of the patient as a whole.

In addition to the above-named variants, there is the further possibility of using a number of X-ray tubes instead of a single one for the purpose of scanning the heart, in which case the incomplete voxel values that are combined to form a complete voxel value can then in turn originate either respectively from detector data generated by a single X-ray tube, or from detector data generated by at least two different X-ray tubes.

Whereas the method of at least one embodiment variants previously set forth firstly refer only to a single voxel value, it is also possible for a multiplicity of considered voxels to be grouped in accordance with a slice, preferably an axial slice, through the patient or the heart, and calculated in a groupwise fashion.

It is provided in a further variant of at least one embodiment of the method that during the calculation of a second cardiac phase period the incomplete voxel values not associated with the second cardiac phase period are subtracted, if appropriate in a weighted fashion, from the complete voxel values of the first cardiac phase period, and only the voxel values that are new by comparison with the first cardiac phase period are added up, if appropriate in a weighted fashion. To simplify, this corresponds to removing data of an earlier period and adding data of a later period, that is to say to exchanging two data packets. If there is a very small number of the individual subsegments with the aid of which the incomplete voxels are calculated, a substantial saving of computing time can thereby be achieved once more.

It is possible in principle to carry out the sole reconstruction of all the incomplete voxel values continuously over the entire temporal and spatial scan, although it is also within the scope of the invention when a phase period of the cardiac cycles that is smaller than the overall cardiac cycle is prescribed for the sole reconstruction of all the incomplete voxel values. This becomes interesting, for example, when only a specific cardiac cycle region is calculated and, for example, no images are to be calculated in the surroundings of the R wave, in which the movement of the heart is too fast anyway. A reduction in the computing time can thereby be effected in accordance with the reduced phase period by comparison with the overall cardiac cycle.

In the case of at least one embodiment of the inventive method, it is advantageous when equally large segments from the detector data are used for the reconstruction of all the incomplete voxel values. Furthermore, it is particularly advantageous here to select the segment size in such a way that an integral multiple yields at least one 180° segment, that is to say at least one half revolution. The weighting otherwise required in adding up the incomplete voxel values is then superfluous with this variant.

At least one embodiment of the inventive method can be carried out in conjunction both with sequential and with spiral scanning, but the use of continuous spiral scanning appears to be particularly favorable, since this means continuous scanning of the entire examination volume.

It is possible to make use of an ECG derivative, for example, as pulse-correlated clock signal, or else a pressure pulse derivative of the mechanical pulse such as is used, for example, in some keep fit equipment for the purpose of displaying the heart rate.

In accordance with the previously outlined basic idea of at least one embodiment of the invention, the inventor also proposes a computer tomography unit for producing X-ray CT pictures of a patient's beating heart that has an apparatus for rotational scanning of the patient with the aid of at least one X-ray tube and at least one detector, the detector continuously detecting the attenuation of the X-rays and outputting it as detector output data to a control and arithmetic logic unit, as well as a device for detecting a pulse-correlated clock signal and a system composed of at least one arithmetic logic unit and programs or program modules that execute the steps of the previously described method during operation.

BRIEF DESCRIPTION OF THE DRAWINGS

Additional features and advantages of the invention emerge from the following description of example embodiments with reference to the drawings.

The invention is described in more detail below with reference to the example embodiments with the aid of the figures, it being pointed out that only the elements essential to the immediate understanding of the invention are shown. The following reference symbols are used here: 1: computed tomography unit; 2: X-ray tube; 3: detector/multirow detector; 4: system axis; 5: housing; 6: displaceable patient couch; 7: patient; 8: ECG lead; 9: control and arithmetic logic unit; 10: control and data line; 11: focus position; 11': second focus position; 12: X-ray beam through a voxel; 12': X-ray beam through a voxel from the second focus position; 13: scanning spiral; 14: voxel; 15.x: scanning beams of a focus through a voxel onto the detector; 16: ECG derivative; 17: R wave; 18: retrospective time offset relative to the R wave; $T_1$: first starting instant of the image calculation; $T_2$: second starting instant of the image calculation; $V_x$: incomplete voxel values; Z: system axis; U: voltage; t: time.

In detail.

DETAILED DESCRIPTION OF THE EXAMPLE EMBODIMENTS

Figure 1:
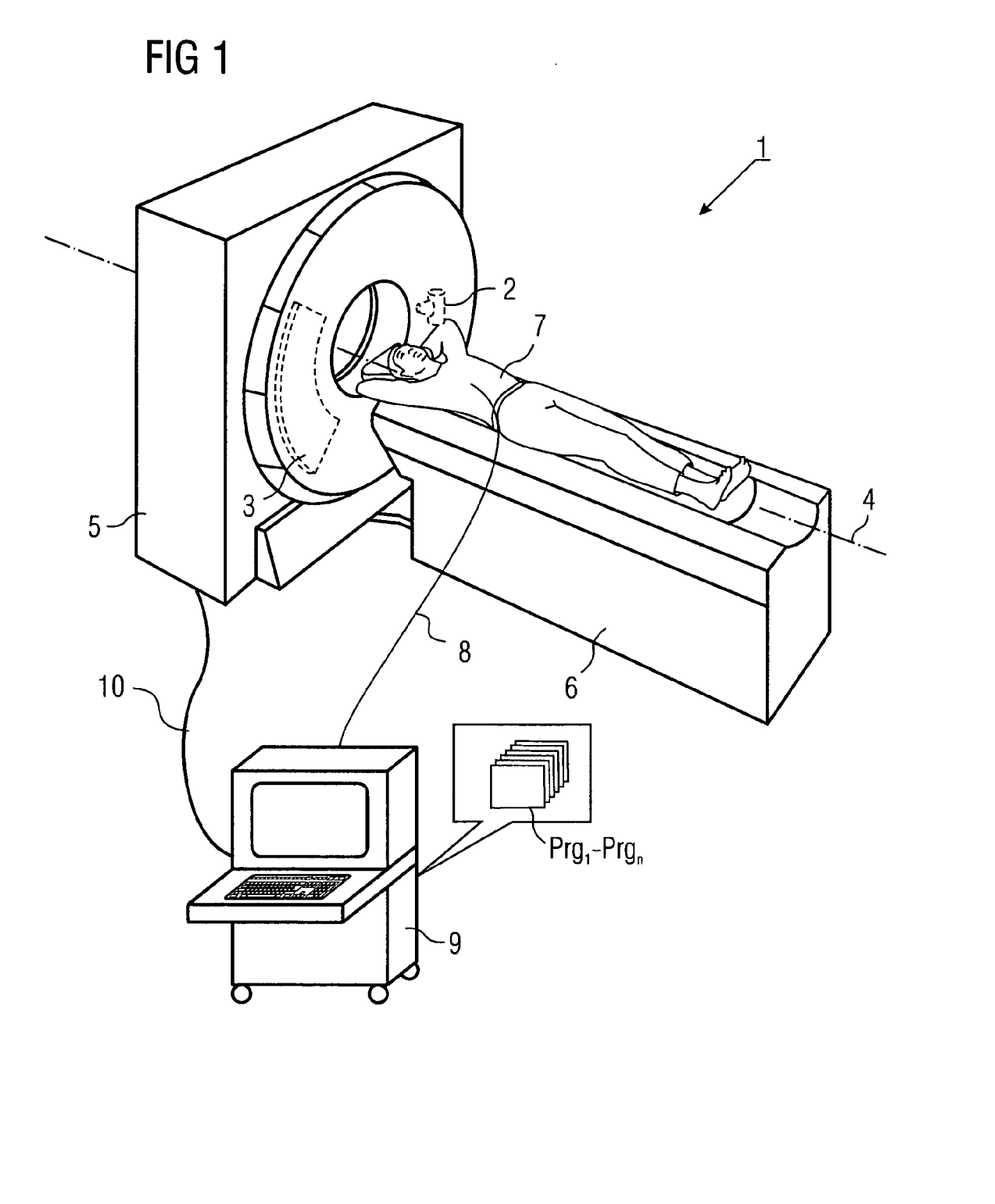
FIG. 1 shows a computed tomography unit for carrying out at least one embodiment of the inventive method.

FIG. 1 shows a computed tomography unit 1 that is used for spiral scanning. To this end, an X-ray tube 2 with a detector 3 situated opposite is located on a gantry having a housing 5. Located between the detector 3 and X-ray tube 2 is an opening through which a patient 7 can be pushed during the rotation of the X-ray tube 2 and of the detector 3 with the aid of a displaceable couch 6. Spiral scanning is produced relative to the patient by the rotational movement of the tube/detector system and simultaneous continuous displacement of the patient 7 in the direction of the system axis 4. This movement is controlled by a control and arithmetic logic unit 9, while the arithmetic logic unit 9 also collects and processes detector output data via the control/data line 10 during the scanning operation. In addition, during scanning the cardiac activity of the patient is recorded via an ECG data line 8 by an ECG integrated in the control and arithmetic logic unit 9, and stored in a fashion correlated with the recorded detector data.

The programs $Prg_1$-$Prg_n$ stored in the control and arithmetic logic unit carry out the arithmetic operations and inventive method steps.

Figure 2:
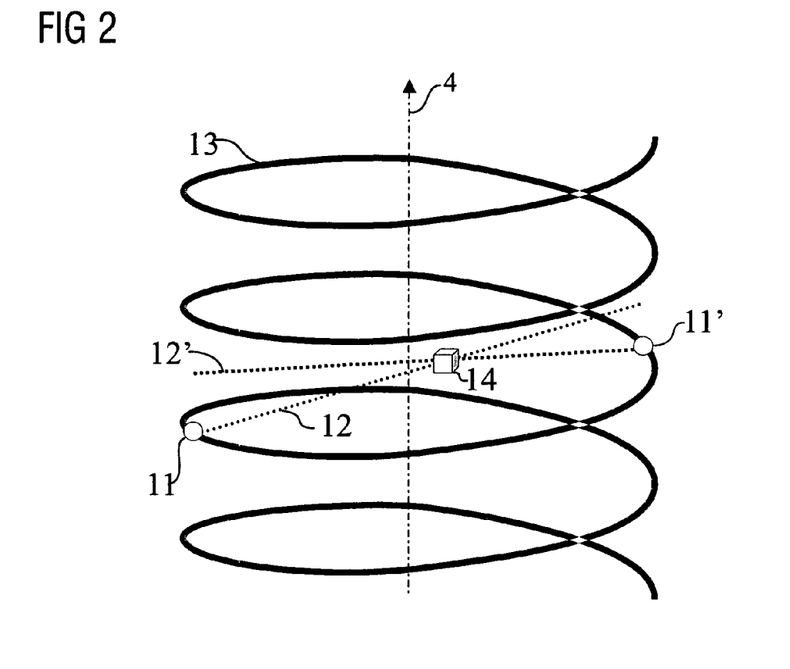
FIG. 2 shows a schematic of spiral scanning of a voxel in the examination object.

The relative movement of a focus 11 of X-ray tube 2 about a patient on a spiral track 13 is illustrated in FIG. 2. By way of elucidation, this figures shows a voxel 14 that is intended to illustrate a specific volume element in the patient. Shown through this voxel 14 are two beams 12 and 12' that penetrate the voxel starting from a focus position 11 or 11', respectively, and impinge on a detector situated opposite.

The complete reconstruction of the voxel value for the voxel 14 requires the detector information that extends over an angle of rotation of 180° overall. However, it is also possible to carry out a voxel reconstruction over subsegments smaller than 180°, in which case incomplete voxel values are calculated. Thus, if, for example, a 180° segment is divided into three subsegments of 60° each, incomplete voxel values are reconstructed over these subsegments of 60° each, and these incomplete voxel values are subsequently added together, a complete voxel value is obtained that is identical to a voxel value reconstructed over 180°.

Figure 3:
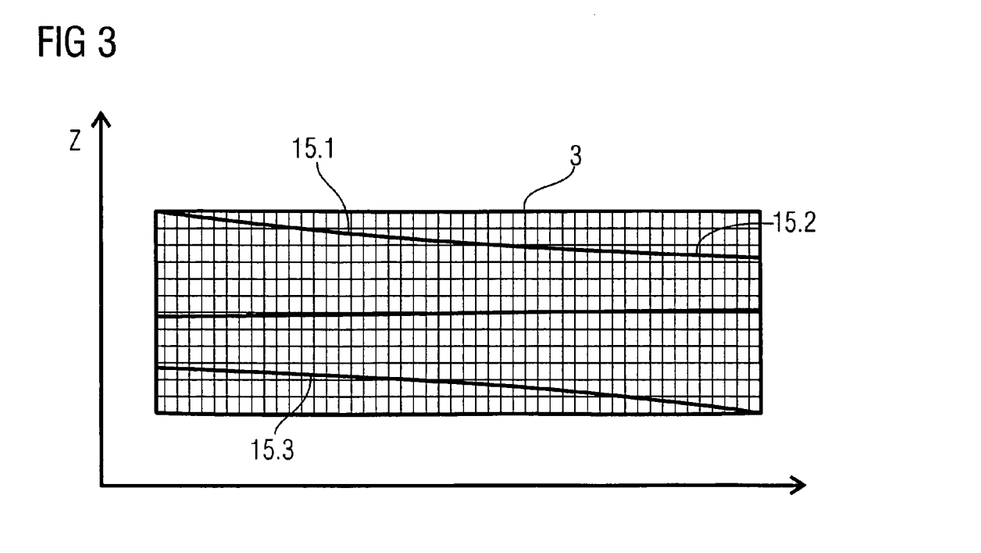
FIG. 3 shows variants of the course of a scanning beam through a voxel on a multirow detector.

Three example traces of such a beam that emanates from a focus 11, penetrates a specific voxel and strikes the opposite side of a detector are illustrated in FIG. 3 by the paths 15.1-15.3. Thus, according to at least one embodiment of the invention, these projections of a voxel that are produced during scanning onto a detector are subdivided into partial sections or segments that correspond to angles smaller than 180°.

It is advantageous here when a subdivision is performed in such a way that integral multiples of the subsegments yield exactly 180° overall. 60° subsegments are used in the following FIGS. 4-7, and so in each case three incompletely reconstructed voxels can be superposed in order to yield a complete voxel value. Of course, it is also possible to perform much smaller divisions.

Figure 4:
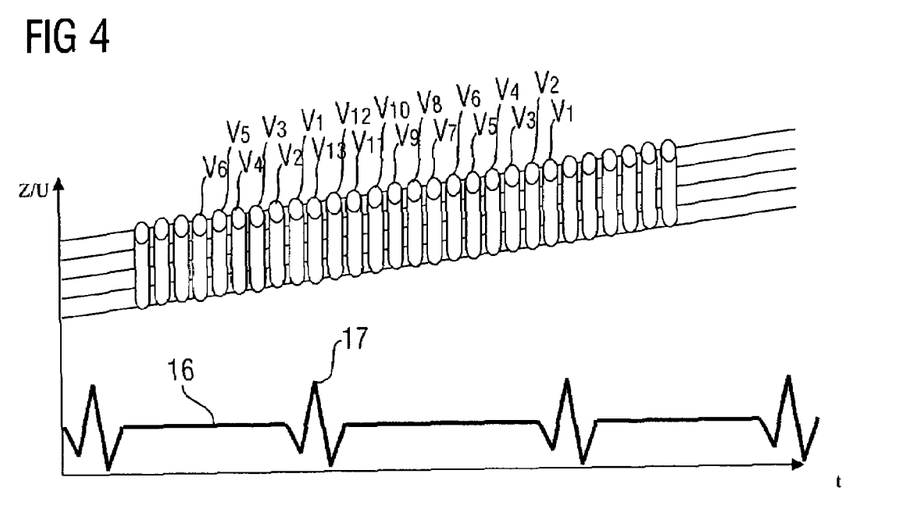
FIG. 4 shows a schematic of voxelwise and segmentwise reconstruction packets, including an ECG derivative therebelow.
Figure 5:
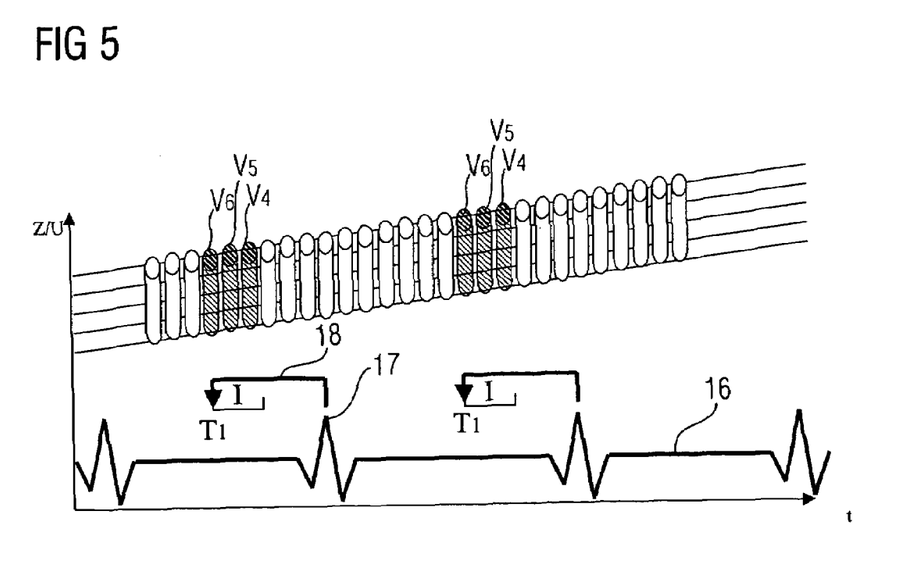
FIG. 5 shows a selection of reconstruction packets from FIG. 4 in order to display a specific scanning instant.

In order to elucidate this situation, FIG. 4 shows a diagram in which the subvoxel values $V_1$-$V_{13}$ of a cardiac cycle are plotted against time, while an ECG derivative 16 is illustrated therebelow in a time-correlated fashion. With reference to the ECG derivative, the voltage potential U is plotted on the ordinate, and the Z-coordinate is illustrated with reference to the subvoxels $V_x$. The feed running ahead as time expires in the direction of the system axis is illustrated by the continuous rise in the subvoxel values $V_x$.

FIG. 5 thereunder once again shows the schematic illustration of the continuous reconstruction of incomplete voxels $V_x$, although here the arrow 18 has determined an initial instant $T_1$ of a first cardiac phase I, emanating retrospectively from an R wave 17 in the ECG, in which the aim is to calculate the complete voxel value. In accordance with the stipulation that the subsegment is to sweep over 60° in order to reconstruct an incomplete voxel value $V_x$, there is thus a need for three subsegments in order to form a complete voxel value. The voxel values $V_6$, $V_5$ and $V_4$ are correspondingly required in this example in order to form the complete voxel value.

Figure 6:
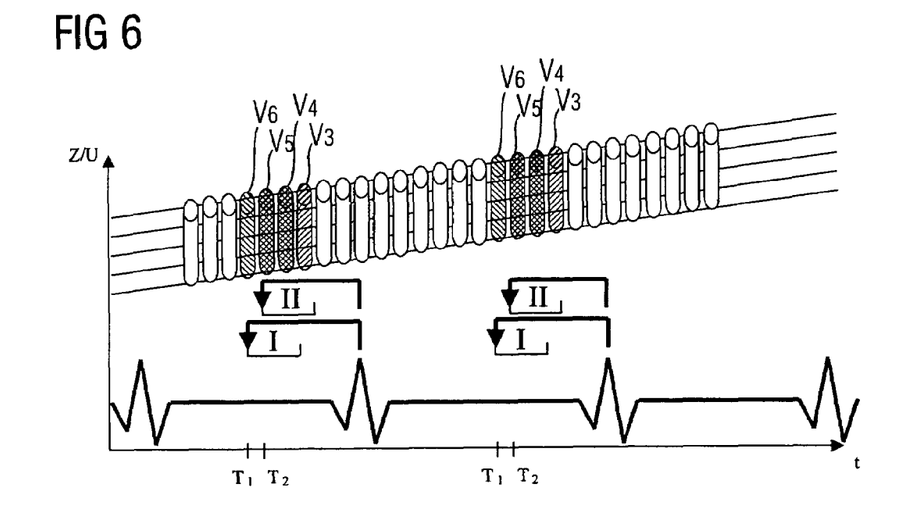
FIG. 6 shows a schematic of the temporally sequential displacement for the purpose of calculating voxel values.

Since the computationally expensive reconstruction operations have already been terminated, the complete voxel value at the instant $T_1$ can be produced with a very small computational outlay. If the operator would now like to redetermine the complete voxel values from the instant $T_2$—corresponding to the second cardiac cycle phase—instead of from the instant $T_1$, that is to say a somewhat later instant, then—as shown in FIG. 6—all that is required is to add up the incomplete voxel values $V_5$, $V_4$ and $V_3$ instead of the incomplete voxel values $V_6$, $V_5$ and $V_4$. This arithmetic operation can, in turn, be carried out very easily and requires a relatively slight arithmetic capability in the computer used.

Such a mode of procedure is illustrated by FIG. 6. Shown starting at the instants $T_1$ and $T_2$ are the two cardiac phases I and II which are assigned the incomplete voxel values $V_4$-$V_6$ and $V_3$-$V_5$. As described above, the complete voxel value of the second cardiac phase II can also be calculated from the complete voxel value of the first cardiac phase I by subtracting the incomplete voxel value $V_6$ and adding the incomplete voxel value $V_3$ without carrying out a new reconstruction.

Thus, if it is desired to run a film sequence over the cardiac cycle, it is possible, for example, to begin at the incomplete voxel $V_{13}$—after completion of prior reconstruction of the incomplete voxels—and to add up sequentially triple packets $V_{n-0}$ to $V_{n-2}$ with n=13 to n=3, and to form complete voxel values by calculation. If this is carried out over a specific volume or a slice, a film sequence is produced that illustrates the movement of the heart. The arithmetic operations required remain slight in this case.

Thus, in accordance with the method illustrated, it is possible starting from a first early instant within the cardiac cycle to calculate successively a multiplicity of voxel values in a temporally sequential fashion, and thus also to display the entire volume sequentially in time with little computational outlay.

If the subsegments used, from which incomplete voxels are calculated, become substantially smaller, for example in the region of 30 degrees and less, instead of adding up all the required subvoxel values anew in each case from the previously calculated complete voxel, it can be advantageous merely to extract an incomplete voxel situated on one side with reference to the time axis and to add a new incomplete voxel to the residual value on the other side, the result once again being a considerable saving in computing time. If data are available from a number of X-ray tubes, these can thus also be recorded in an appropriate way in the available data pool of incomplete voxels, the operator now having a simple possibility involving little computation of selecting combinations optimum for imaging from the data that are present.

It is pointed out in particular at this juncture that the method according to at least one embodiment of the invention is not restricted to calculation of a single voxel, but that the calculation of the incomplete voxels can, of course, also be performed in groupwise fashion such that, for example, a complete image slice can be calculated from a multiplicity of individual voxels, or an image volume can be calculated simultaneously in the way previously described.

It is pointed out furthermore, that it is also possible in accordance with at least one embodiment of the inventive method for calculating complete voxel values to make use of incomplete voxel values from a number of cardiac cycles of the same cardiac phase. There is a corresponding improvement in the time resolution in this case.

Figure 7:
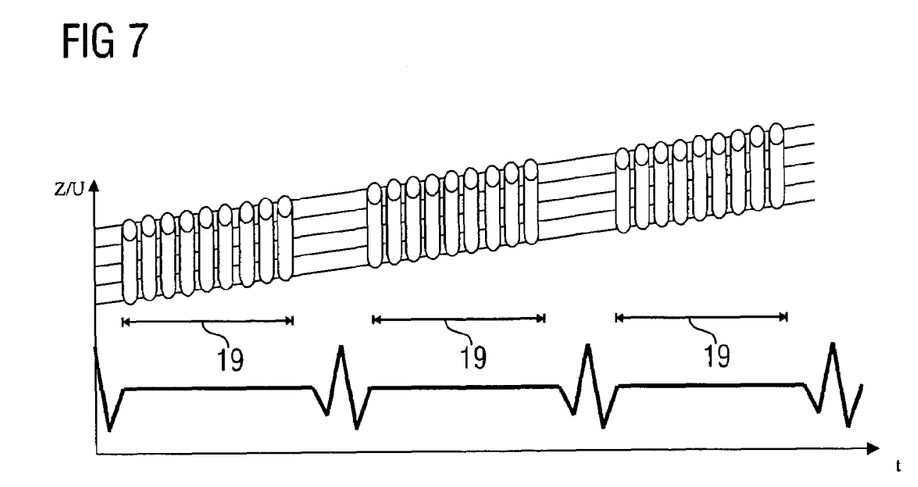
FIG. 7 shows a schematic of the selection of the reconstruction phase regions.

FIG. 7 is intended to illustrate again that it is not absolutely necessary to reconstruct the entire range of the cardiac cycle, but that it suffices to reconstruct a certain cardiac phase region 19 that is of interest, doing so firstly with the aid of the incomplete voxels, it being possible to omit time intervals in which it is clear from the start that sufficiently sharp imagings are not possible because of excessive movement of the heart.

It goes without saying that the abovementioned features of embodiments of the invention can be used not only in the combination respectively specified, but also in other combinations or on their own without departing from the framework of the invention.

Overall, at least one embodiment of the invention thus presents a method and/or computed tomography unit for producing computed tomograms of a patient's beating heart by means of voxelwise reconstruction of volume data records from prescribed cardiac cycle phases, in the case of which a multiplicity of voxelwise partial reconstructions are firstly calculated from projection segments substantially smaller than 180° in accordance with small cardiac phase sections. The complete voxel data that cover overall at least 180° and originate from a preselected cardiac phase are subsequently summed up per cardiac phase to be considered from the pool of the incomplete reconstructed voxel data.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing computed tomograms of a patient's beating heart, comprising:
   rotating at least one X-ray tube relative to and about the patient and about a system axis, to scan the patient;
   recording a pulse-correlated clock signal of the patient to determine a cycle phase and a cycle of the heart;
   continuously detecting attenuation of the X-rays during the rotation of the at least one X-ray tube and outputting detected data;
   dividing the scanning volume into small three-dimensional voxels, and searching, in relation to each voxel, for beams, and detected output data generated therefrom, that intersect the voxel;
   reconstructing incomplete voxel values from the voxel-referred detected output data, the detected data used per voxel reconstruction including a scanning segment that corresponds only to a fraction of a half revolution;
   assigning each of the reconstructed incomplete voxel values a time stamp from the cycle phase, where the cycle from which the reconstructed incomplete voxel value has been reconstructed is determinable;
   storing each of the assigned reconstructed incomplete voxel values;
   adding up, for a first calculation of at least one complete voxel value from a first cardiac phase period, the stored reconstructed incomplete voxel values from the first cardiac phase period, until a sum of the scanning segments of the stored reconstructed incomplete voxel values corresponds to at least 180°; and
   adding up, for a second calculation of at least one complete voxel value from a second cardiac phase period, the stored reconstructed incomplete voxel values from the second cardiac phase period, until a sum of the scanning segments of the stored reconstructed incomplete voxel values corresponds to at least 180°, the first cardiac phase period and the second cardiac phase period overlapping.

2. The method as claimed in claim 1, wherein the stored reconstructed incomplete voxel values combined to form a complete voxel value, originate from one cardiac cycle.

3. The method as claimed in claim 2, wherein incomplete voxel values are reconstructed from detector data of only one cardiac cycle.

4. The method as claimed in claim 1, wherein the stored reconstructed incomplete voxel values combined to form a complete voxel value, originate from at least two consecutive cardiac cycles.

5. The method as claimed in claim 4, wherein incomplete voxel values are reconstructed from detector data of only one cardiac cycle.

6. The method as claimed in claim 1, wherein the incomplete voxel values are reconstructed from detector data of only one cardiac cycle.

7. The method as claimed in claim 1, wherein the incomplete voxel values are reconstructed from detector data of a plurality of consecutive cardiac cycles.

8. The method as claimed in claim 1, wherein the stored reconstructed incomplete voxel values combined to form a complete voxel value, originate respectively from detector data generated by an X-ray tube.

9. The method as claimed in claim 1, wherein the stored reconstructed incomplete voxel values combined to form a complete voxel value, originate respectively from detector data generated by at least two different X-ray tubes.

10. The method as claimed in claim 1, wherein a multiplicity of complete voxel values are grouped in accordance with a slice through at least one of the patient or the heart, and calculated in a groupwise fashion.

11. The method as claimed in claim 1, wherein, during the calculation of a second cardiac phase period, the incomplete voxel values not associated with the second cardiac phase period are subtracted-from the complete voxel values of the first cardiac phase period, and only the voxel values that are new in comparison to the first cardiac phase period are added up.

12. The method as claimed in claim 11, wherein, the stored reconstructed incomplete voxel values are subtracted from the complete voxel values in a weighted fashion and the new voxel values are added up in a weighted fashion.

13. The method as claimed in claim 1, wherein the sole reconstruction of all the incomplete voxel values is carried out continuously over the entire temporal and spatial scan.

14. The method as claimed in claim 1, wherein a phase period of the cardiac cycles that is smaller than the overall cardiac cycle is prescribed for the sole reconstruction of all the incomplete voxel values.

15. The method as claimed in claim 1, wherein segments from the detector data are used for the reconstruction of all the incomplete voxel values.

16. The method as claimed in claim 15, wherein the segment size is selected such that an integral multiple yields a 180° segment.

17. The method as claimed in claim 1, wherein the method is used in conjunction with spiral scanning.

18. The method as claimed in claim 1, wherein the method is used in conjunction with sequential scanning.

19. The method as claimed in claim 1, wherein an ECG derivative is used as pulse-correlated clock signal.

20. The method as claimed in claim 1, wherein a pressure pulse derivative is used as pulse-correlated clock signal.

21. A computed tomography unit for producing computed tomograms of a patient's beating heart, comprising:
an apparatus for rotational scanning of the patient with the aid of at least one X-ray tube and at least one detector that continuously detects the attenuation of the X-rays, outputted as detector output data to at least one arithmetic logic unit;
means for detecting a pulse-correlated clock signal; and
a system including the at least one arithmetic logic unit and at least one of programs and program modules, to execute the method of claim 1 during operation.

22. The method as claimed in claim 1, wherein a multiplicity of complete voxel values are grouped in accordance with an axial slice, through at least one of the patient and the heart, and calculated in a groupwise fashion.

23. A computer-readable medium including a computer program, adapted to, when executed on a computer, cause the computer to carry out the method as claimed in claim 1.

24. A computer program product, including the computer readable medium of claim 23.

25. A computer readable medium including program segments for, when executed on a computer, causing the computer to implement the method of claim 1.

26. A computed tomography unit for producing computed tomograms of a patient's beating heart, comprising:
means for rotating at least one X-ray tube relative to and about the patient and about a system axis, to scan the patient;
means for recording a pulse-correlated clock signal of the patient to determine the cycle phase and the cycle of the heart;
means for continuously detecting attenuation of the X-rays during the rotation of the at least one X-ray tube and outputting detected data;
means for dividing the scanning volume into small three-dimensional voxels, and searching, in relation to each voxel, for beams, and detected output data generated therefrom, that intersect the voxel;
means for reconstructing incomplete voxel values from the voxel-referred detected output data, the detected data used per voxel reconstruction including a scanning segment that corresponds only to a fraction of a half revolution;
means for assigning each of the reconstructed incomplete voxel values a time stamp from the cycle phase and the cycle from which the reconstructed incomplete voxel value has been reconstructed is determinable;
means for storing each of the assigned reconstructed incomplete voxel values;
means for adding up, for a first calculation of at least one complete voxel value from a first cardiac phase period, the stored reconstructed incomplete voxel values from the first cardiac phase period, until a sum of the scanning segments of the reconstructed incomplete voxel values corresponds to at least 180°; and
means for adding up, for a second calculation of at least one complete voxel value from a second cardiac phase period, the stored reconstructed incomplete voxel values from the second cardiac phase period, until a sum of the scanning segments of the reconstructed incomplete voxel values corresponds to at least 180°, the first cardiac phase period and the second cardiac phase period overlapping.

27. A method for producing a computed tomogram of a patient's beating heart by voxelwise reconstruction of volume data records from prescribed cardiac cycle phases, the method comprising:
calculating a multiplicity of voxelwise partial reconstructions from projection segments substantially smaller than 180° in accordance with small cardiac phase segments to form a pool of incomplete reconstructed voxel data; and
storing the pool of incomplete reconstructed voxel data;
summing up complete voxel data, that covers at least 180° and originates from a preselected cardiac phase, for each of at least two cardiac phases to be considered from the pool of stored incomplete reconstructed voxel data, with a first cardiac phase period and at least one other cardiac phase period overlapping.

28. A computer readable medium including program segments for, when executed on a computer, causing the computer to implement the method of claim 27.

* * * * *